US012575782B2

(12) United States Patent
Samadani et al.

(10) Patent No.: US 12,575,782 B2
(45) Date of Patent: *Mar. 17, 2026

(54) METHOD AND SYSTEM FOR DETECTING CONCUSSION

(71) Applicant: OCULOGICA INC., New York, NY (US)

(72) Inventors: Rosina Samadani, New York, NY (US); Daniel O. Sanderson, New Richmond, WI (US); Joel D. Sanderson, Woodbury, MN (US)

(73) Assignee: Oculogica Inc., New York, NY (US)

( * ) Notice: Subject to any disclaimer, the term of this patent is extended or adjusted under 35 U.S.C. 154(b) by 1093 days.

This patent is subject to a terminal disclaimer.

(21) Appl. No.: 17/474,146

(22) Filed: Sep. 14, 2021

(65) Prior Publication Data

US 2022/0039734 A1 Feb. 10, 2022

Related U.S. Application Data

(63) Continuation of application No. 15/897,704, filed on Feb. 15, 2018, now Pat. No. 11,141,095.

(60) Provisional application No. 62/460,412, filed on Feb. 17, 2017.

(51) Int. Cl.
*A61B 5/00* (2006.01)
*A61B 5/16* (2006.01)

(52) U.S. Cl.
CPC ............ *A61B 5/4064* (2013.01); *A61B 5/162* (2013.01); *A61B 5/163* (2017.08); *A61B 5/746* (2013.01)

(58) Field of Classification Search
CPC ........ A61B 5/4064; A61B 5/162; A61B 5/163
See application file for complete search history.

(56) References Cited

U.S. PATENT DOCUMENTS

| | | | | |
|---|---|---|---|---|
| 10,482,333 B1* | 11/2019 | el Kaliouby | ........... | G16H 20/70 |
| 2007/0105071 A1* | 5/2007 | Weatherhead | ........... | A61B 5/16 |
| | | | | 434/81 |
| 2008/0227073 A1* | 9/2008 | Bardsley | ................ | G09B 23/34 |
| | | | | 434/267 |
| 2008/0255949 A1* | 10/2008 | Genco | ....................... | A61B 5/16 |
| | | | | 705/14.4 |
| 2013/0278631 A1* | 10/2013 | Border | ................ | G06F 3/04842 |
| | | | | 345/633 |
| 2015/0145777 A1* | 5/2015 | He | ........................ | G06V 40/193 |
| | | | | 348/78 |
| 2015/0190050 A1* | 7/2015 | Samadani | .............. | A61B 3/113 |
| | | | | 600/558 |
| 2016/0073874 A1* | 3/2016 | Tsai | ........................ | A61B 5/398 |
| | | | | 351/210 |
| 2016/0278716 A1* | 9/2016 | Samadani | .............. | A61B 3/085 |
| 2017/0172408 A1* | 6/2017 | Samadani | .............. | A61B 3/024 |
| 2017/0367633 A1* | 12/2017 | Samadani | ............ | A61B 5/7275 |

* cited by examiner

*Primary Examiner* — Sean P Dougherty

(74) *Attorney, Agent, or Firm* — SLEMAN & LUND LLP

(57) ABSTRACT

A method for identifying an occurrence of a concussion in a subject involves capturing eye blink raw data from at least one eye of the subject. The method next involves analyzing the eye blink raw data to generate at least a first subject specific eye blink metric and determining that a significant difference exists between the first subject specific eye blink metric and a predefined normal value. Next, the occurrence of the concussion in the subject may be identified, based on determining that the significant difference exists.

20 Claims, 1 Drawing Sheet

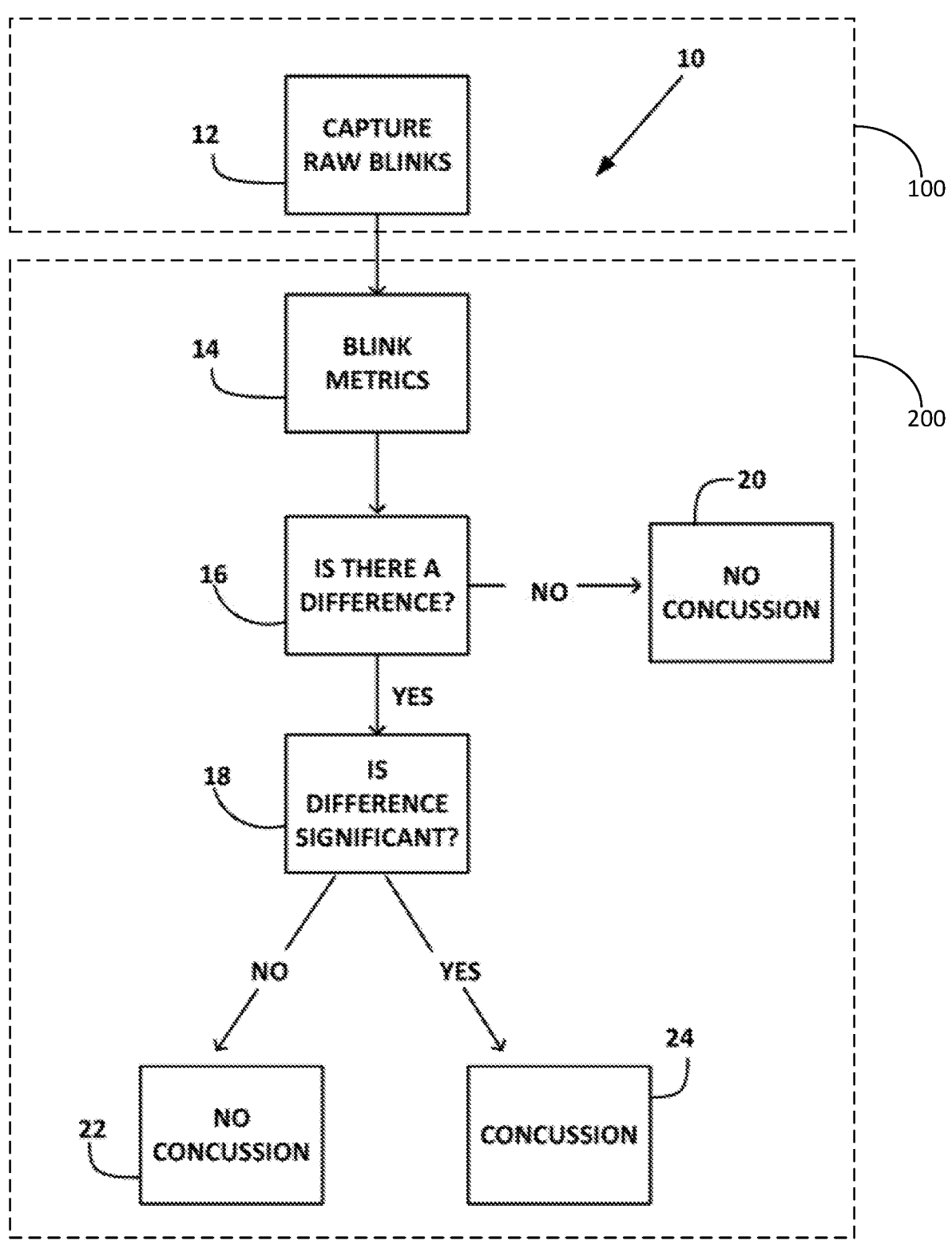

METHOD AND SYSTEM FOR DETECTING CONCUSSION

CROSS-REFERENCE TO RELATED APPLICATIONS

The present application is a continuation of U.S. patent application Ser. No. 15/897,704, filed Feb. 15, 2019, entitled, "METHOD AND SYSTEM FOR DETECTING CONCUSSION," and claims the benefit of U.S. Provisional Patent Application No. 62/460,412, filed Feb. 17, 2017, entitled, "METHODS AND KITS FOR DETECTING CONCUSSION." The disclosures of these applications are hereby incorporated by reference in its entirety into the present application.

TECHNICAL FIELD

This application is related to medical devices, systems and methods. More specifically, the application is related to a method and system for detecting, screening for and/or quantifying concussion in a subject using eye blink data.

BACKGROUND

Concussions are a significant and common medical problem, with adverse health consequences that are continuing to be discovered. Concussions may occur, for example, from automobile and motorcycle accidents, sports, falls, and many other causes. Centers for Disease Control reports show that the number of reported concussions has doubled over the last ten years. The American Academy of Pediatrics has reported that emergency room visits for concussions in children aged eight to thirteen have doubled, and concussions have risen two hundred percent among teens aged fourteen to nineteen in the last decade. While a first concussion can prove problematic, the second or third head impact can cause permanent long-term brain damage. Cumulative sports concussions are shown to increase the likelihood of catastrophic head injury leading to permanent neurologic disability by 39 percent. Among the many challenges with properly treating concussions is the fact that they can often be hard to diagnose quickly and effectively.

Therefore, it would be highly advantageous to have improved methods and systems for detecting the occurrence of a concussion in a subject. It would also be ideal to be able to assess, quantify or analyze the severity of a detected concussion. At least some of these objectives will be discussed in the present application.

BRIEF SUMMARY

All publications, patent applications, patents and other reference material mentioned in this application are hereby incorporated by reference in their entirety herein. For example, the following patent applications are incorporated by reference: Patent Cooperation Treaty Patent Application Nos. PCT/US2013/033672, filed Mar. 25, 2013; and PCT/US2014/042645, filed Jun. 17, 2014, and U.S. Provisional Patent Application No. 61/835,927, filed Jun. 17, 2013; 61/881,014, filed Sep. 23, 2013; 61/929,238, filed Jan. 20, 2014; 62/032,769, filed Aug. 4, 2014; and 62/065,057, filed Oct. 17, 2014. In addition, the materials, methods and examples are only illustrative and are not intended to be limiting. The citation of references herein is not to be construed as an admission that the references are prior art to the present invention.

In one aspect of this application, a method for identifying an occurrence of a concussion in a subject involves: capturing eye blink raw data from at least one eye of the subject; analyzing the eye blink raw data to generate at least a first subject specific eye blink metric; determining that a significant difference exists between the first subject specific eye blink metric and a predefined normal value; and identifying the occurrence of the concussion in the subject, based on determining that the significant difference exists.

Capturing the eye blink raw data, for example, may include capturing an indication of which of the subject's eyes a blink occurred in, a start timestamp of a blink, an end timestamp of a blink, and/or a duration of a blink. In some embodiments, capturing the eye blink raw data involves tracking eye blinks of one or both eyes of the subject using an eye tracking system. Tracking eye blinks may involve showing a video stimulus to the subject, where the video stimulus may include a moving aperture, a stationary aperture or both.

The eye blink metric may be one or more of the following: a total number of blinks detected in the subject's left eye, a total number of blinks detected in the subject's right eye, an average number of blinks per a period detected in the subject's left eye, an average number of blinks per a period detected in the subject's right eye, a median duration or a mean duration of blinks detected in the subject's left eye, a median duration or a mean duration of blinks detected in the subject's right eye, a portion of left eye blinks that are overlapped by right eye blinks, a portion of right eye blinks that are overlapped by left eye blinks, a variance of gaps between blinks in the subject's left eye, a variance of gaps between blinks in the subject's right eye, a number of blinks in the subject's left eye that do not have a corresponding blink in the subject's right eye, a number of blinks in the subject's right eye that do not have a corresponding blink in the subject's left eye, a median or mean of a time difference from when a left blink starts to when a right blink starts, a median or mean of a time difference from when a right blink starts to when a left blink starts, a variance of the time difference from when a left blink starts to when a right blink starts, a variance of the time difference from when a right blink starts to when a left blink starts, a median or a mean of a time difference from when a left blink ends to when a right blink ends, and a median or a mean of a time difference from when a right blink ends to when a left blink ends. Other metrics may be generated in other embodiments, and these examples are not intended to be limiting.

The predefined normal value may come from any of a number of different sources, such as but not limited to a baseline eye blink metric measured at a previous time for the subject, a second subject specific eye blink metric, a control eye blink metric, and/or an expected normal value based on previously acquired data. In some embodiments, the determining step may involve comparing blinks of the subject's left eye to blinks of the patient's right eye. In some embodiments, the determining step may involve comparing blinks of one or both of the subject's eyes to baseline blinks of one or both of the subject's eyes. In some embodiments, the determining step may involve comparing blinks of one or both of the subject's eyes to control blinks of one or both eyes of one or more control subjects.

Optionally, the method may involve a further step of determining if the difference between the first subject specific eye blink metric and the predefined normal value is sufficiently significant to indicate the occurrence of a concussion. In some embodiments, the determining step may involve determining that the subject has a z-score above 2.

In some embodiments, the determining step may involve calculating at least one of a standard deviation or a p value for the first subject specific eye blink metric compared to the predefined normal value.

The method may also involve providing an output to a user indicating the identification of the occurrence of the concussion. Such an output may include a concussion score, an audio alert, a visual alert, numerical data, a certainty factor and/or any other suitable output.

In another aspect of the present disclosure, a method for identifying an occurrence of a concussion in a subject may involve: analyzing eye blink raw data captured from the subject to generate at least a first subject specific eye blink metric; determining that a difference exists between the first subject specific eye blink metric and a baseline eye blink metric measured at a previous time for the subject, a second subject specific eye blink metric, and/or a control eye blink metric; and identifying the occurrence of the concussion in the subject, based on determining that the difference exists. In some embodiments, the method may also involve capturing the eye blink raw data from at least one eye of the subject. All the aspects and features described above may be applied to various embodiments of this method.

In another aspect of this application, a system for diagnosing, identifying and/or quantifying a concussion in a subject may include an eye tracking device and a computer processor coupled with the eye tracking device and containing instructions for performing a method for identifying an occurrence of a concussion in a subject. The method may be the same as or similar to the methods described above.

In yet another aspect of the disclosure, a non-transitory computer-readable medium may have instructions stored thereon for diagnosing, identifying and/or quantifying a concussion in a subject. The instructions, when executed by a computer processor, operate to receive eye blink raw data from at least one eye of the subject and perform a method the same as, or similar to, the methods described above.

These and other aspects and embodiments are described in further detail below, in reference to the attached drawing figures.

BRIEF DESCRIPTION OF THE DRAWINGS

FIG. 1 is a flow diagram illustrating a method for diagnosing, identifying and/or quantifying a concussion in a subject, according to one embodiment.

DETAILED DESCRIPTION

Referring to FIG. 1, a method 10 for diagnosing, quantifying and/or identifying concussion in a subject according to one embodiment is illustrated. As described in further detail below, the method 10 may be performed by a computer processor 200, which may be incorporated into an eye tracking system 100 or may be separate from an eye tracking system 100. In some embodiments, for example, eye tracking/eye blink data may be received in a processor 200 on a stand-alone device, such as a computer, laptop computer, tablet computer, smart phone or the like. For the method and system embodiments described below, the assumption will be that the computer processor resides on the eye tracking device itself 100, but that is not necessarily the case for all embodiments.

The concussion diagnostic method 10 may first involve collecting, receiving or "capturing" raw blink data 12 from one or both eyes of a subject. In one embodiment, this eye blink data is collected via an eye tracking system, such as currently known eye tracking systems or any suitable eye tracking system developed in the future. The raw eye blink data may pertain to one or both of the subject's eyes. Examples of raw blink data 12 that might be captured for each blink include, but are not limited to, which eye a blink occurred in (i.e., the subject's left eye or right eye), a start timestamp of a blink, an end timestamp of a blink, and a duration of a blink.

Next, the computer processor receives the raw blink data/eye tracking data and analyzes the raw data to develop (or "compute") one or more eye blink metrics 14 that describe the subject's blinks in some way. In some embodiments, the first step—i.e., the eye tracking/raw blink data capturing step 12—might not be a part of the method. In other words, the method in some embodiments starts with the step of receiving the raw data and analyzing it to generate metrics 14. This application contemplates both embodiments—i.e., where the method includes capturing the raw blink data 12 and where the method starts after the raw blink data has already been generated.

Examples of the eye blink metrics 14 that may be provided by the method include, but are not limited to: a total number of blinks detected in the subject's left eye, a total number of blinks detected in the subject's right eye, an average number of blinks per a period detected in the subject's left eye, an average number of blinks per a period detected in the subject's right eye, a median or mean duration of blinks detected in the subject's left eye, a median or mean duration of blinks detected in the subject's right eye, a portion of left eye blinks that are overlapped by right eye blinks, a portion of right eye blinks that are overlapped by left eye blinks, a variance of gaps between blinks in the subject's left eye, a variance of gaps between blinks in the subject's right eye, a number of blinks in the subject's left eye that do not have a corresponding blink in the subject's right eye, a number of blinks in the subject's right eye that do not have a corresponding blink in the subject's left eye, a median or mean of a time difference from when a left blink starts to when a right blink starts, a median or mean of a time difference from when a right blink starts to when a left blink starts, a variance of the time difference from when a left blink starts to when a right blink starts, a variance of the time difference from when a right blink starts to when a left blink starts, a median or mean of a time difference from when a left blink ends to when a right blink ends, and a median or mean of a time difference from when a right blink ends to when a left blink ends.

The blink overlap metric refers to the portion of time that blinks in the other eye overlaps the blinks in the specified eye. The nth blink for the other eye may be correlated to the blink that overlaps the current blink. For example, a previous blink may be detected in one eye but not the other, causing the index of the overlapping blinks to be different for each eye. Blink gap variance may be defined for both eyes and describes the variance of the amount of time between each blink in the specified eye. Blink start sync is the median of the time between when a blink in the left eye begins and the right eye begins. Only blinks that overlap are included in this calculation. The nth blink for the other eye may be correlated to the blink that overlaps the current blink. For example, a previous blink may be detected in one eye but not the other, causing the index of the overlapping blinks to be different for each eye. These are merely examples of eye blink metrics that may be used, according to various embodiments.

The next step in the method is to determine if there is a difference 16 between the measured eye blink metric(s) for the subject and some predefined "normal" value for one or more metrics. If there is a difference, this might indicate the occurrence of a concussion in the patient. The predefined normal value may be derived from any of a number of different sources or combinations of sources. For example, the normal value may be derived from: (1) known concussion values, from studies or data collected from multiple test subjects; (2) a database of blink data; (3) one or more baseline values measured on the subject himself/herself at a previous time; or (4) one or more control values measured on a control subject (or multiple control subjects). In some embodiments, the difference that is analyzed may be between the subject's right and left eyes, in which case the normal value might be a measurement of one of the subject's eyes that is known to be currently normal. Again, any of the metrics listed above may be used in this step 16.

In some embodiments, for example, the value of each blink metric is compared to expected values for both non-concussed and concussed people. Measured values may be compared to non-concussed people separately, or in combination. Measured values may also be compared using various types of conditions. For example, the distance of the measured value or combined values to the expected value or combined values may be used to compute a score indicating how strongly this metric(s) suggests a concussion. In another embodiment, if the measured value or combined values to the expected value or combined values is greater than the expected value or combined values for concussed/non-concussed people, the metric may suggest the person is either concussed/not concussed. Alternatively, in another embodiment, if the measured value or combined values to the expected value or combined values is less than the expected value or combined values for concussed/non-concussed people, the metric may suggest the person is either concussed/not concussed. In another example, if the measured value or combined values to the expected value or combined values falls within (or in some cases, outside) the expected range or combined ranges, the metric may suggest of a concussion. Some embodiments may employ machine learning. For example, the measured value or combined values may be input to a machine learning model trained on various states of concussion to predict if the person is either concussed/not concussed. Based on what the comparisons suggests, the device will report that the subject is concussed/not-concussed or the device may report a score indicating the likelihood of being concussed.

If the processor determines 16 there is no measurable difference, then a further determination is made 20 that the subject has not suffered a concussion. If the processor determines 16 that there is a difference, then the computer processor next determines if the difference is significant 18. If not, then the processor determines the subject has not suffered a concussion 22. If the difference is significant, then the processor determines the subject has suffered a concussion 24. In some embodiments, the initial determining step 16 may be eliminated, and instead the initial determination may simply be whether a significant difference exists 18. Further details regarding this method are provided below. According to various embodiments, the output of the computer processor may be provided to a user in any suitable form. For example, an eye tracking system that includes the processor (or a separate computing system in some embodiments) may alert the user with an indicator light, sound and/or readout that a concussion has occurred. Additionally or alternatively, the processor may provide a "score," which may be numerical or alpha numeric and which indicates whether the subject suffered a concussion, and if so, how severe the concussion was. Any type of indicator, or combination of indicators, may be provided, according to various embodiments.

In another aspect of the present application, a system for diagnosing, quantifying and/or identifying concussion in a subject may include a computing system with a processor and instructions on the processor for performing the method described immediately above. The computer system or computing device may include the processor, a display, an eye blink tracker component, etc. The computing system may include a bus or other communication component for communicating information and a processor or processing circuit coupled to the bus for processing information. The computing system can also include one or more processors or processing circuits coupled to the bus for processing information. The computing system also includes main memory, such as a random access memory (RAM) or other dynamic storage device, coupled to the bus for storing information, and instructions to be executed by the processor. Main memory can also be used for storing position information, temporary variables, or other intermediate information during execution of instructions by the processor. The computing system may further include a read only memory (ROM) or other static storage device coupled to the bus for storing static information and instructions for the processor. A storage device, such as a solid state device, magnetic disk or optical disk, is coupled to the bus for persistently storing information and instructions.

The computing system may be coupled via the bus to a display, such as a liquid crystal display, or active matrix display, for displaying information to a user. An input device, such as a keyboard including alphanumeric and other keys, may be coupled to the bus for communicating information and command selections to the processor. In another implementation, the input device has a touch screen display. The input device can include a cursor control, such as a mouse, a trackball, or cursor direction keys, for communicating direction information and command selections to the processor and for controlling cursor movement on the display.

According to various implementations, the methods described herein can be implemented by the computing system in response to the processor executing an arrangement of instructions contained in main memory. Such instructions can be read into main memory from another computer-readable medium, such as the storage device. Execution of the arrangement of instructions contained in main memory causes the computing system to perform the illustrative processes described herein. One or more processors in a multi-processing arrangement may also be employed to execute the instructions contained in main memory. In alternative implementations, hard-wired circuitry may be used in place of or in combination with software instructions to effect illustrative implementations. Thus, implementations are not limited to any specific combination of hardware circuitry and software.

According to the methods described, tracking eye blinks may be performed using any suitable device, such as, for example, an Eyelink® 1000 binocular eye tracker (500 Hz sampling, SR Research). The eye tracking movement samples may be obtained at any suitable frequency, such as for instance, 10 Hz to 10,000 Hz or more. The subject may be positioned an appropriate distance from the device, such as, for example, 10, 20, 30, 40, 50, 55, 60, 70, 80, 90 cm or more, or even a meter or more from the device screen. In some instances, the subject's head may be stabilized, such as, for instance by using a chinrest or similar stabilizing mechanism. The subject may be seated or reclining. Preferably, the presentation monitor of the device is adjusted so as to substantially match the subject's gaze direction. The tracking eye blinks frequency and duration may be performed for a total of, for example, 30, 60, 90, 120, 150, 180, 200, 220, 240, 270, 300, 330, 360, 400, 450, 500 seconds or more, or for 5, 10, 15, 20, 25, 30, 45, 60, or 90 minutes or more. As such, according to the methods provided, 1,000, 5,000, 10,000, 20,000, 25,000, 50,000, 75,000, 100,000, 150,000, 200,000, 250,000, 300,000 or more samples of eye position may be obtained. Similarly, tracking eye blinks may be performed using a video oculography device, such as, for instance, goggles, or using a web-cam based tracking system.

According to the methods described, analyzing eye blinks may be performed by any suitable means. In some instances, a stimulus and an analysis stream are provided that allows interpreting raw eye position data. Preferably, a device is adapted into a novel mobile system that may analyze eye blinks close in time or substantially concurrent to the eye blinks.

According to the methods described, eye blinks may be tracked in response to a visual stimulus. In some instances, the visual stimulus may be, for instance, a video such as a music video that is stationary or may move, for instance clockwise, along the outer edge, of a computer monitor. In some instances, such a video may be provided starting at the upper or lower, left or right hand corners, of a screen. The visual stimulus such as a video, e.g. a music video, may be provided in a substantially square aperture with an area of approximately 10, 12, 14, 16, 18, 20, or 25 degrees, for example, approximately $\frac{1}{10}$, $\frac{1}{8}$, $\frac{1}{6}$, $\frac{1}{5}$, or $\frac{1}{4}$ the size of the screen. The visual stimulus, such as, for example a music video, may play substantially continuously during the eye blinks tracking, and it may in some instances move across the screen at a relatively or substantially constant speed. For instance, such a visual stimulus, for instance, a music video may cover each edge of a monitor in about 2, 5, 10, 15, 20, 30, 45 or 60 seconds. Therefore, in some instances, a full cycle may take, for instance, 10, 20, 30, 40, 50, 60, 75, 100, 120, 150, 180 seconds. Multiple cycles of such a visual stimulus, for instance a music video may be played, for instance, 1, 2, 3, 4, 5, 6, 7, 8, 9, 10, 12, 15, 20 or more full cycles.

As such, the visual stimulus may be provided and the eye blinks be tracked, for a total of, for example, 30, 60, 90, 120, 150, 180, 200, 220, 240, 270, 300, 330, 360, 400, 450, 500 seconds or more. In instances where the visual stimulus is in the form of a video, a countdown video may be played in the starting position for, for instance, 5, 10, 15, 20, 25, or 30 seconds or more before beginning the visual stimulus, e.g. video, to provide subjects sufficient time to orient to the visual stimulus. Likewise, the visual stimulus, for instance a video, may be continued for an addition 2, 5, 10, 15, 20, 30, 45 or 60 seconds or so after the eye blinks tracking is performed to reduce or substantially avoid boundary effects. The same result could be obtained by having the visual stimulus moving over any distance x relative to any amount of time t.

According to the methods described, comparing eye blinks of a first eye of the subject to eye blinks of a second eye of the subject, may be performed by analyzing data. According to the methods described, identifying the subject as having eye blinks significantly different from the control, or identifying the subject as having eye blinks of a first eye that is significantly different from eye blinks of a second eye, may be performed using a z-score. For example, a z-score of 2 may be used as a significance threshold. Subjects with z-scores above, for instance, 2 in either or both, or 1, 2, 3, or 4 sides or arms of the figures may be judged to have significant disturbances of ocular motility. Similarly, identifying the subject as having eye blinks significantly different from the control, or identifying the subject as having eye blinks of a first eye that is significantly different from eye blinks of a second eye, may be performed by assessing whether it has or there is a difference that exceeds a predetermined threshold.

Applicant believes this to be a full and accurate description of various embodiments of a method and system for diagnosing, identifying and/or quantifying concussion in a subject. The foregoing description is of embodiments only and is not intended to limit the scope of the claims that follow.

The invention claimed is:

1. A method for identifying an occurrence of a concussion in a subject, the method comprising:

seating the subject in front of a display at a distance of between 10 and 90 cm, and presenting a visual stimulus on the display;

capturing eye blink raw data from two eyes of the subject in response to the visual stimulus using an eye tracking device having a camera at a frequency greater than 500 Hz to obtain a sample over at least 30 seconds;

analyzing, via a processor, a measure of how often blinks from the two eyes overlap over a period of time when subjected to a common visual stimulus on the display; and identifying, via the processor, the occurrence of a concussion in the subject based on the measure.

2. The method of claim 1, wherein capturing the eye blink raw data comprises capturing at least one of an indication of which of the subject's eyes a blink occurred in, a start timestamp of a blink, an end timestamp of a blink, or a duration of a blink.

3. The method of claim 1, wherein presenting a visual stimulus on the display comprises showing a video stimulus to the subject, and wherein the video stimulus comprises at least one of a moving aperture or a stationary aperture.

4. The method of claim 1, further comprising determining that a statistically significant difference exists between the first subject specific eye blink metric and a predefined normal value, via the processor.

5. The method of claim 4, wherein the predefined normal value is selected from the group consisting of a baseline eye blink metric measured at a previous time for the subject, a second subject specific eye blink metric, a control eye blink metric, and an expected normal value based on previously acquired data.

6. The method of claim 4, wherein the determining step comprises comparing blinks of the subject's left eye to blinks of the patient's right eye.

7. The method of claim 4, wherein the determining step comprises comparing blinks of one or both of the subject's eyes to baseline blinks of one or both of the subject's eyes.

8. The method of claim 4, wherein the determining step comprises comparing blinks of one or both of the subject's eyes to control blinks of one or both eyes of one or more control subjects.

9. The method of claim 4, wherein the determining step comprises determining that the subject has a z-score above 2.

10. The method of claim 4, wherein the determining step comprises calculating at least one of a standard deviation or a p value for the first subject specific eye blink metric compared to the predefined normal value.

11. The method of claim 1, further comprising providing an output to a user indicating the identification of the occurrence of the concussion, wherein the output is selected from the group consisting of a concussion score, an audio alert, a visual alert, numerical data and a certainty factor.

12. The method of claim 1, wherein presenting a visual stimulus on the display comprises showing a music video that moves across the display at a constant speed.

13. The method of claim 1, wherein presenting a visual stimulus on the display comprises showing a music video that moves along four outer edges of the display.

14. The method of claim 1, further comprising analyzing at least one additional metric, wherein the at least one additional metric includes a total number of blinks detected in the subject's left eye and a total number of blinks detected in the subject's right eye over the period of time.

15. The method of claim 1, further comprising analyzing at least one additional metric, wherein the at least one additional metric includes an average number of blinks detected in the subject's left eye, and an average number of blinks detected in the subject's right eye over the period of time.

16. The method of claim 1, further comprising analyzing at least one additional metric, wherein the at least one additional metric includes a median duration or a mean duration of blinks detected in the subject's left eye, and a median duration or a mean duration of blinks detected in the subject's right eye.

17. The method of claim 1, further comprising analyzing at least one additional metric, wherein the at least one additional metric includes a median or a mean of a time difference from when a left blink ends to when a right blink ends, and a median or a mean of a time difference from when a right blink ends to when a left blink ends.

18. The method of claim 1, wherein the eye tracking device is a non-contact device that is spaced at least 30 centimeters away from the subject.

19. A method for identifying an occurrence of a concussion in a subject, the method comprising:

presenting a visual stimulus on a display;

capturing eye blink raw data from two eyes of the subject in response to the visual stimulus using an eye tracking device having a camera at a frequency greater than 500 Hz to obtain a sample over at least 30 seconds;

counting a number of blinks in a first eye of the subject that do not have a corresponding blink in a second eye of the subject; and identifying, via a processor, the occurrence of a concussion in the subject based on the counted number of blinks.

20. The method of claim 19, further comprising analyzing the data after removing the nonoverlapping blinks.

\* \* \* \* \*